United States Patent
Chappa et al.

(10) Patent No.: US 7,833,548 B2
(45) Date of Patent: *Nov. 16, 2010

(54) BIOACTIVE AGENT RELEASE COATING AND CONTROLLED HUMIDITY METHOD

(75) Inventors: Ralph A. Chappa, Prior Lake, MN (US); Robert W. Hergenrother, Eden Prairie, MN (US); Aron B. Anderson, Minnetonka, MN (US); Linh V. Tran, Brooklyn Park, MN (US); Laurie R. Lawin, New Brighton, MN (US); Ronald F. Ofstead, Maplewood, MN (US)

(73) Assignee: Surmodics, Inc., Eden Prairie, MN (US)

( * ) Notice: Subject to any disclaimer, the term of this patent is extended or adjusted under 35 U.S.C. 154(b) by 998 days.

This patent is subject to a terminal disclaimer.

(21) Appl. No.: 11/207,380

(22) Filed: Aug. 19, 2005

(65) Prior Publication Data
US 2007/0248637 A1      Oct. 25, 2007

Related U.S. Application Data

(63) Continuation of application No. 10/175,210, filed on Jun. 18, 2002, now Pat. No. 7,097,850.

(51) Int. Cl.
*A61K 9/14*       (2006.01)
(52) U.S. Cl. .................................... 424/486
(58) Field of Classification Search ........... None
See application file for complete search history.

(56) References Cited

U.S. PATENT DOCUMENTS

| | | | |
|---|---|---|---|
| 4,069,307 A | 1/1978 | Higuchi | |
| 4,292,965 A | 10/1981 | Nash | |
| 4,391,797 A | 7/1983 | Folkman | |
| 4,409,206 A | 10/1983 | Stricker | |
| 4,603,152 A | 7/1986 | Laurin | |
| 4,623,346 A | 11/1986 | von Bittera | |
| 4,627,852 A | 12/1986 | von Bittera | |

(Continued)

FOREIGN PATENT DOCUMENTS

CA      2320259      4/1999

(Continued)

OTHER PUBLICATIONS

Chien, "Novel Drug Delivery Systems", INforma Health Care, Chapter 1, p. 29, 1991.*

(Continued)

*Primary Examiner*—Carlos A Azpuru
(74) *Attorney, Agent, or Firm*—Pauly, Devries Smith & Deffner, L.L.C.

(57) ABSTRACT

A coating composition in the form of a one or multi-part system, and method of applying such a composition under conditions of controlled humidity, for use in coating device surfaces to control and/or improve their ability to release bioactive agents in aqueous systems. The coating composition is particularly adapted for use with medical devices that undergo significant flexion and/or expansion in the course of their delivery and/or use, such as stents and catheters. The composition includes the bioactive agent in combination with a first polymer component such as polyalkyl(meth)acrylate, polyaryl(meth)acrylate, polyaralkyl(meth)acrylate, or polyaryloxyalkyl(meth)acrylate and a second polymer component such as poly(ethylene-co-vinyl acetate).

18 Claims, 3 Drawing Sheets

U.S. PATENT DOCUMENTS

| | | |
|---|---|---|
| 4,693,887 A | 9/1987 | Shah |
| 4,722,906 A | 2/1988 | Guire |
| 4,768,507 A | 9/1988 | Fischell |
| 4,826,759 A | 5/1989 | Guire |
| 4,867,968 A | 9/1989 | Allen |
| 4,916,193 A | 4/1990 | Tang |
| 4,959,217 A | 9/1990 | Sanders |
| 4,968,539 A | 11/1990 | Aoyagi |
| 4,973,493 A | 11/1990 | Guire |
| 4,979,959 A | 12/1990 | Guire |
| 4,994,071 A | 2/1991 | MacGregor |
| 5,002,582 A | 3/1991 | Guire |
| 5,019,096 A | 5/1991 | Fox |
| 5,114,719 A | 5/1992 | Sabel |
| 5,165,952 A | 11/1992 | Solomon |
| 5,180,366 A | 1/1993 | Woods |
| 5,217,492 A | 6/1993 | Guire |
| 5,221,698 A | 6/1993 | Amidon |
| 5,248,732 A | 9/1993 | Drzewinski |
| 5,258,041 A | 11/1993 | Guire |
| 5,263,992 A | 11/1993 | Guire |
| 5,304,121 A | 4/1994 | Sahatjian |
| 5,310,559 A | 5/1994 | Shah |
| 5,342,348 A | 8/1994 | Kaplan |
| 5,356,433 A | 10/1994 | Rowland |
| 5,380,299 A | 1/1995 | Fearnot |
| 5,414,075 A | 5/1995 | Swan |
| 5,419,760 A | 5/1995 | Narciso |
| 5,431,790 A | 7/1995 | Nesburn et al. |
| 5,437,656 A | 8/1995 | Shikani |
| 5,443,505 A | 8/1995 | Wong |
| 5,447,724 A | 9/1995 | Helmus |
| 5,449,382 A | 9/1995 | Dayton |
| 5,451,424 A | 9/1995 | Solomon |
| 5,464,650 A | 11/1995 | Berg |
| 5,466,233 A | 11/1995 | Weiner |
| 5,474,783 A | 12/1995 | Miranda et al. |
| 5,512,055 A | 4/1996 | Domb |
| 5,512,329 A | 4/1996 | Guire |
| 5,525,348 A | 6/1996 | Whitbourne |
| 5,545,208 A | 8/1996 | Wolfe |
| 5,563,056 A | 10/1996 | Swan |
| 5,567,417 A | 10/1996 | Sasisekharan et al. |
| 5,569,463 A | 10/1996 | Helmus |
| 5,578,075 A | 11/1996 | Dayton |
| 5,591,227 A | 1/1997 | Dinh |
| 5,605,696 A | 2/1997 | Eury |
| 5,607,475 A | 3/1997 | Cahalan et al. |
| 5,607,687 A | 3/1997 | Bezwada et al. |
| 5,609,629 A | 3/1997 | Fearnot |
| 5,618,552 A | 4/1997 | Bezwada et al. |
| 5,620,698 A | 4/1997 | Bezwada et al. |
| 5,624,411 A | 4/1997 | Tuch |
| 5,624,975 A | 4/1997 | Valencia |
| 5,633,343 A | 5/1997 | Bezwada et al. |
| 5,637,113 A | 6/1997 | Tartaglia |
| 5,637,460 A | 6/1997 | Swan |
| 5,639,851 A | 6/1997 | Bezwada et al. |
| 5,641,501 A | 6/1997 | Cooper et al. |
| 5,651,968 A | 7/1997 | Good |
| 5,651,986 A | 7/1997 | Brem |
| 5,656,286 A | 8/1997 | Miranda |
| 5,660,692 A | 8/1997 | Nesburn et al. |
| 5,674,241 A | 10/1997 | Bley |
| 5,676,972 A | 10/1997 | Galiatsatos et al. |
| 5,688,900 A | 11/1997 | Cooper et al. |
| 5,703,200 A | 12/1997 | Bezwada et al. |
| 5,705,181 A | 1/1998 | Cooper et al. |
| 5,714,360 A | 2/1998 | Swan |
| 5,714,551 A | 2/1998 | Bezwada |
| 5,722,424 A | 3/1998 | Engelson |
| 5,731,087 A | 3/1998 | Fan et al. |
| 5,741,551 A | 4/1998 | Guire |
| 5,744,515 A | 4/1998 | Clapper |
| 5,766,242 A | 6/1998 | Wong |
| 5,773,019 A | 6/1998 | Ashton |
| 5,783,502 A | 7/1998 | Swanson |
| 5,824,049 A | 10/1998 | Ragheb |
| 5,824,072 A | 10/1998 | Wong |
| 5,837,313 A | 11/1998 | Ding |
| 5,840,059 A | 11/1998 | March |
| 5,858,653 A | 1/1999 | Duran |
| 5,859,150 A | 1/1999 | Jamiolkowski |
| 5,877,224 A | 3/1999 | Brocchini |
| 5,879,697 A | 3/1999 | Ding |
| 5,886,026 A | 3/1999 | Hunter |
| 5,895,407 A | 4/1999 | Jayaraman |
| 5,897,911 A | 4/1999 | Loeffler |
| 5,899,935 A | 5/1999 | Ding |
| 5,902,475 A | 5/1999 | Trozera |
| 5,919,477 A | 7/1999 | Bevan et al. |
| 5,942,555 A | 8/1999 | Swanson |
| 5,951,586 A | 9/1999 | Berg |
| 5,958,446 A | 9/1999 | Miranda et al. |
| 5,980,972 A | 11/1999 | Ding |
| 5,981,298 A | 11/1999 | Chudzik |
| 5,985,354 A | 11/1999 | Mathiowitz et al. |
| 5,997,517 A | 12/1999 | Whitbourne |
| 6,001,386 A | 12/1999 | Ashton |
| 6,007,833 A | 12/1999 | Chudzik |
| 6,013,099 A | 1/2000 | Dinh |
| 6,042,875 A | 3/2000 | Ding |
| 6,074,660 A | 6/2000 | Jamiolkowski et al. |
| 6,077,698 A | 6/2000 | Swan |
| 6,077,916 A | 6/2000 | Laurencin et al. |
| 6,090,995 A | 7/2000 | Reich |
| 6,096,070 A | 8/2000 | Ragheb |
| 6,099,562 A | 8/2000 | Ding |
| 6,110,483 A * | 8/2000 | Whitbourne et al. ......... 424/423 |
| 6,120,536 A | 9/2000 | Ding |
| 6,120,847 A | 9/2000 | Yang |
| 6,121,027 A | 9/2000 | Clapper |
| 6,129,933 A | 10/2000 | Oshlack |
| 6,143,037 A | 11/2000 | Goldstein |
| 6,153,252 A | 11/2000 | Hossainy |
| 6,156,345 A | 12/2000 | Chudzik |
| 6,156,373 A | 12/2000 | Zhong |
| 6,214,370 B1 * | 4/2001 | Nelson et al. ................ 424/425 |
| 6,214,901 B1 | 4/2001 | Chudzik |
| 6,217,895 B1 | 4/2001 | Guo |
| 6,235,306 B1 | 5/2001 | Miranda |
| 6,251,136 B1 | 6/2001 | Guruwaiya |
| 6,254,634 B1 | 7/2001 | Anderson |
| 6,258,121 B1 | 7/2001 | Yang et al. |
| 6,284,305 B1 | 9/2001 | Ding et al. |
| 6,287,285 B1 | 9/2001 | Michal |
| 6,303,148 B1 | 10/2001 | Hennink et al. |
| 6,309,669 B1 | 10/2001 | Setterstrom et al. |
| 6,325,807 B1 | 12/2001 | Que |
| 6,331,313 B1 | 12/2001 | Wong |
| 6,344,035 B1 | 2/2002 | Chudzik |
| 6,348,152 B1 | 2/2002 | Kawahara |
| 6,358,556 B1 | 3/2002 | Ding |
| 6,368,586 B1 | 4/2002 | Jacob |
| 6,395,029 B1 | 5/2002 | Levy |
| 6,399,704 B1 | 6/2002 | Laurin |
| 6,423,092 B2 | 7/2002 | Datta et al. |
| 6,447,796 B1 | 9/2002 | Vook et al. |
| 6,451,373 B1 | 9/2002 | Hossainy |
| 6,497,691 B1 | 12/2002 | Bevins |
| 6,506,411 B2 | 1/2003 | Hunter |
| 6,511,749 B1 | 1/2003 | Mathiowitz et al. |
| 6,517,520 B2 | 2/2003 | Chang |
| 6,537,312 B2 | 3/2003 | Datta et al. |

| | | |
|---|---|---|
| 6,544,544 B2 | 4/2003 | Hunter |
| 6,545,097 B2 | 4/2003 | Pinchuk |
| 6,548,078 B2 | 4/2003 | Guo |
| 6,548,569 B1 | 4/2003 | Williams et al. |
| 6,565,872 B2 | 5/2003 | Wu et al. |
| 6,569,441 B2 | 5/2003 | Kunz |
| 6,585,764 B2 | 7/2003 | Wright |
| 6,589,546 B2 | 7/2003 | Kamath |
| 6,620,194 B2 | 9/2003 | Ding et al. |
| 6,653,426 B2 | 11/2003 | Alvarado |
| 6,673,453 B2 | 1/2004 | Beavers |
| 6,682,553 B1 | 1/2004 | Webler |
| 6,689,803 B2 | 2/2004 | Hunter |
| 6,713,081 B2 | 3/2004 | Robinson et al. |
| 6,730,313 B2 | 5/2004 | Helmus |
| 6,773,888 B2 | 8/2004 | Li et al. |
| 6,776,796 B2 | 8/2004 | Falotico et al. |
| 6,780,424 B2 | 8/2004 | Claude |
| 6,787,179 B2 | 9/2004 | Timm |
| 6,790,228 B2 | 9/2004 | Hossainy |
| 6,800,073 B2 | 10/2004 | Palasis |
| 6,824,559 B2 | 11/2004 | Michal |
| 6,838,493 B2 | 1/2005 | Williams et al. |
| 6,846,841 B2 | 1/2005 | Hunter |
| 6,867,247 B2 | 3/2005 | Williams et al. |
| 7,008,667 B2 | 3/2006 | Chudzik |
| 7,097,850 B2 * | 8/2006 | Chappa et al. ............... 424/423 |
| 7,125,577 B2 | 10/2006 | Chappa |
| 2001/0029351 A1 | 10/2001 | Falotico |
| 2002/0005206 A1 | 1/2002 | Falotico |
| 2002/0007213 A1 | 1/2002 | Falotico |
| 2002/0007214 A1 | 1/2002 | Falotico |
| 2002/0007215 A1 | 1/2002 | Falotico |
| 2002/0013298 A1 | 1/2002 | Hunter |
| 2002/0018795 A1 | 2/2002 | Whitbourne |
| 2002/0032434 A1 | 3/2002 | Chudzik |
| 2002/0032477 A1 | 3/2002 | Helmus |
| 2002/0051730 A1 | 5/2002 | Bodnar |
| 2002/0051731 A1 | 5/2002 | Fukami |
| 2002/0071902 A1 | 6/2002 | Ding |
| 2002/0091433 A1 | 7/2002 | Ding |
| 2002/0111590 A1 | 8/2002 | Davila |
| 2002/0133183 A1 | 9/2002 | Lentz |
| 2002/0138048 A1 | 9/2002 | Tuch |
| 2002/0164374 A1 | 11/2002 | Jackson et al. |
| 2002/0165608 A1 | 11/2002 | Llanos et al. |
| 2002/0188037 A1 | 12/2002 | Chudzik |
| 2003/0031780 A1 | 2/2003 | Chudzik et al. |
| 2003/0039689 A1 | 2/2003 | Chen et al. |
| 2003/0045924 A1 | 3/2003 | Datta et al. |
| 2003/0065377 A1 | 4/2003 | Davila et al. |
| 2003/0083646 A1 | 5/2003 | Sirhan |
| 2003/0094736 A1 | 5/2003 | Qin |
| 2003/0097088 A1 | 5/2003 | Pacetti et al. |
| 2003/0105245 A1 | 6/2003 | Amsden et al. |
| 2003/0157187 A1 | 8/2003 | Hunter |
| 2003/0158598 A1 | 8/2003 | Ashton et al. |
| 2003/0171496 A1 | 9/2003 | Pinchuk et al. |
| 2003/0203000 A1 | 10/2003 | Schwarz et al. |
| 2003/0203003 A1 | 10/2003 | Nelson et al. |
| 2003/0204168 A1 | 10/2003 | Bosma et al. |
| 2003/0207856 A1 | 11/2003 | Tremble |
| 2003/0232087 A1 | 12/2003 | Lawin |
| 2003/0232122 A1 | 12/2003 | Chappa |
| 2003/0235603 A1 | 12/2003 | Schwarz et al. |
| 2003/0236513 A1 | 12/2003 | Schwarz |
| 2003/0236514 A1 | 12/2003 | Schwarz |
| 2004/0022853 A1 | 2/2004 | Ashton |
| 2004/0030380 A1 | 2/2004 | Shulze et al. |
| 2004/0033251 A1 | 2/2004 | Sparer |
| 2004/0039437 A1 | 2/2004 | Sparer |
| 2004/0047911 A1 | 3/2004 | Lyu |
| 2004/0054104 A1 | 3/2004 | Pacetti |
| 2004/0058056 A1 | 3/2004 | Osaki et al. |
| 2004/0059408 A1 | 3/2004 | Alvarado |
| 2004/0072799 A1 | 4/2004 | Li et al. |
| 2004/0077797 A1 | 4/2004 | Asgarzadeh |
| 2004/0086542 A1 | 5/2004 | Hossainy |
| 2004/0086569 A1 | 5/2004 | Sparer et al. |
| 2004/0098118 A1 | 5/2004 | Granada et al. |
| 2004/0111144 A1 | 6/2004 | Lawin et al. |
| 2004/0115273 A1 | 6/2004 | Sparer et al. |
| 2004/0117006 A1 | 6/2004 | Lewis et al. |
| 2004/0117007 A1 | 6/2004 | Whitbourne et al. |
| 2004/0127978 A1 | 7/2004 | Sparer et al. |
| 2004/0170752 A1 | 9/2004 | Luthra |
| 2004/0175406 A1 | 9/2004 | Schwarz |
| 2004/0202691 A1 | 10/2004 | Richard et al. |
| 2004/0224001 A1 | 11/2004 | Pacetti et al. |
| 2004/0230298 A1 | 11/2004 | Udipi et al. |
| 2004/0234737 A1 | 11/2004 | Pacetti et al. |
| 2004/0243225 A1 | 12/2004 | Ragheb et al. |
| 2004/0253203 A1 | 12/2004 | Hossainy et al. |
| 2005/0004663 A1 | 1/2005 | Llanos et al. |
| 2005/0019371 A1 | 1/2005 | Anderson et al. |
| 2005/0025802 A1 | 2/2005 | Richard et al. |
| 2005/0025830 A1 | 2/2005 | Bruinewoud et al. |
| 2005/0033417 A1 | 2/2005 | Borges |
| 2005/0037047 A1 | 2/2005 | Song et al. |
| 2005/0037048 A1 | 2/2005 | Song et al. |
| 2005/0037052 A1 | 2/2005 | Udipi et al. |
| 2005/0042293 A1 | 2/2005 | Jackson et al. |
| 2005/0064005 A1 | 3/2005 | Dinh et al. |
| 2005/0064011 A1 | 3/2005 | Song et al. |
| 2005/0064038 A1 | 3/2005 | Dinh et al. |
| 2005/0281863 A1 | 12/2005 | Anderson |
| 2006/0013835 A1 | 1/2006 | Anderson |
| 2006/0057277 A1 | 3/2006 | Chappa |
| 2006/0067968 A1 | 3/2006 | Chudzik |
| 2006/0134168 A1 | 6/2006 | Chappa |

FOREIGN PATENT DOCUMENTS

| | | |
|---|---|---|
| EP | 0 281 482 A1 | 7/1988 |
| EP | 0 294 905 A1 | 12/1988 |
| EP | 0 470 569 A1 | 2/1992 |
| EP | 0 543 653 A1 | 6/1993 |
| EP | 0 548 448 | 6/1993 |
| EP | 0 551 182 A1 | 7/1993 |
| EP | 0 631 781 | 7/1993 |
| EP | 0 568 310 A1 | 11/1993 |
| EP | 0 274 846 B1 | 2/1994 |
| EP | 0 604 022 A1 | 6/1994 |
| EP | 0 623 354 A1 | 11/1994 |
| EP | 0 706 376 B1 | 4/1996 |
| EP | 0 716 836 A1 | 6/1996 |
| EP | 0 734 721 A2 | 10/1996 |
| EP | 0 747 069 B1 | 12/1996 |
| EP | 0 879 595 A2 | 4/1998 |
| EP | 1 174 157 A1 | 4/1999 |
| EP | 0 923 953 A2 | 6/1999 |
| EP | 0 945 148 A1 | 9/1999 |
| FR | 2757528 | 6/1998 |
| GB | 1 462 958 | 1/1977 |
| JP | 2036882 A2 | 2/1990 |
| JP | 7-017851 | 1/1995 |
| JP | 08033718 A2 | 2/1996 |
| JP | 09099056 A2 | 4/1997 |
| JP | 09194347 A2 | 7/1997 |
| JP | 2000-511946 | 9/2000 |
| JP | 3406903 | 5/2002 |
| WO | WO 88/02623 | 4/1988 |
| WO | WO 89/05616 | 6/1989 |
| WO | WO 90/00887 | 2/1990 |
| WO | WO 90/01969 | 3/1990 |
| WO | WO 90/13332 | 11/1990 |

| | | |
|---|---|---|
| WO | WO 91/03990 | 4/1991 |
| WO | WO 91/07154 | 5/1991 |
| WO | WO 91/10424 | 7/1991 |
| WO | WO 91/11193 | 8/1991 |
| WO | WO 91/12779 | 9/1991 |
| WO | WO 91/12846 | 9/1991 |
| WO | WO 92/00747 | 1/1992 |
| WO | WO 92/11895 | 7/1992 |
| WO | WO 92/12717 | 8/1992 |
| WO | WO 92/15286 | 9/1992 |
| WO | WO 93/06792 | 4/1993 |
| WO | WO 93/11120 | 6/1993 |
| WO | WO 93/16176 | 8/1993 |
| WO | WO 93/16687 | 9/1993 |
| WO | WO 93/17669 | 9/1993 |
| WO | WO 94/11032 | 5/1994 |
| WO | WO 94/21308 | 9/1994 |
| WO | WO 94/21309 | 9/1994 |
| WO | WO 94/24962 | 11/1994 |
| WO | WO 95/03036 | 2/1995 |
| WO | WO 95/03795 | 2/1995 |
| WO | WO 96/03164 | 2/1996 |
| WO | WO 96/03984 | 2/1996 |
| WO | WO 96/37165 | 11/1996 |
| WO | WO 96/39821 | 12/1996 |
| WO | WO 97/16544 | 5/1997 |
| WO | WO 97/34935 | 9/1997 |
| WO | WO 98/17331 | 4/1998 |
| WO | WO 98/56312 | 12/1998 |
| WO | WO 99/08717 | 2/1999 |
| WO | WO 99/16907 | 4/1999 |
| WO | WO 99/38546 | 8/1999 |
| WO | WO 99/43688 | 9/1999 |
| WO | WO 99/47129 | 9/1999 |
| WO | WO 99/47176 | 9/1999 |
| WO | WO 99/53900 | 10/1999 |
| WO | WO 99/55396 | 11/1999 |
| WO | WO 99/64086 | 12/1999 |
| WO | WO 00/12163 | 3/2000 |
| WO | WO 00/40593 | 7/2000 |
| WO | WO 00/55396 | 9/2000 |
| WO | WO 01/00109 | 1/2001 |
| WO | WO 01/21326 | 3/2001 |
| WO | WO 01/34219 | 5/2001 |
| WO | WO 01/36008 | 5/2001 |
| WO | WO 01/44174 | 6/2001 |
| WO | WO 01/66161 | 9/2001 |
| WO | WO 01/87263 | 11/2001 |
| WO | WO 01/87342 | 11/2001 |
| WO | WO 01/87372 | 11/2001 |
| WO | WO 01/87373 | 11/2001 |
| WO | WO 01/87374 | 11/2001 |
| WO | WO 01/87375 | 11/2001 |
| WO | WO 01/87376 | 11/2001 |
| WO | WO 02/26139 | 4/2002 |
| WO | WO 02/26271 | 4/2002 |
| WO | WO 02/26281 | 4/2002 |
| WO | WO 02/078668 | 10/2002 |
| WO | WO 03/022323 | 3/2003 |
| WO | WO 03/064015 | 8/2003 |
| WO | WO-03/105919 | 12/2003 |
| WO | WO 03/105920 | 12/2003 |
| WO | WO 04/000267 | 12/2003 |
| WO | WO 2004/000384 | 12/2003 |
| WO | WO 2004/009145 | 1/2004 |
| WO | WO 2004/014447 | 2/2004 |
| WO | WO 2004/014448 | 2/2004 |
| WO | WO 2004/014450 | 2/2004 |
| WO | WO 2004/014451 | 2/2004 |
| WO | WO 2004/043441 | 5/2004 |
| WO | WO 2004/098565 | 11/2004 |
| WO | WO2004/112746 | * 12/2004 |
| WO | WO2005097228 | 10/2005 |

OTHER PUBLICATIONS

Influence of Relative Humidity on the Mehcanical and Drug Release Properties of Theophylline Pellets Coated with an Acrylic Polymer Containing Methylparaben as a Non-Traditional Plasticizer, Wu et al, European Journal of Pharmaceutics and Biopharmaceutics, vol. 50, No. 2, Sep. 2000, pp. 277-284(8).*

Munday et al, Changes in Drug Release Rate: Effect of Stress Storage Conditions on Film Coated Mini-Tablets, Summary Drug Development and Industrial Pharmacy 1991, vol. 17, No. 15, pp. 2135-2143, DOI 10.3109/03639049109048539.*

Computer Translation for JP 7-017851 previously cited, Jan. 1995 (publication date), Takao et al.

Riggs, P.D. et al., "Chlorhexidine release from room temperature polymerising methacrylate systems," Biomaterials 21, 2001, pp. 345-351.

Dev, Vishva, et al., Kinetics of Drug Delivery to the Arterial Wall Via Polyurethane Coated Removable Nitinol Stent-Comparative Study of 2 Drugs, Cedars-Sinai Medical Center, Los Angeles, CA., Circulation, vol. 88, No. 4, Part 2, Oct. 1993.

Lambert, Thomas, et al., Localized Arterial Drug Delivery from a Polymer Coated Removable Metallic Stent: Kinetics and Bioactivity of Forskolin, Cedars-Sinai Medical Center, Los Angeles, CA., Circulation, vol. 88, No. 4, Part 2, Oct. 1993.

Sasabe et al., "Dielectric Relaxations and Electrical Conductivities of Poly(alkyl Methacrylates) under High Pressure", J. Polymer science 6(1968) pp. 1401-1418.

Database WPI Section Ch, Week 197837, Derwent Publications Ltd., London, GB; JP 53 090697 A (Japanese Geon Co Ltd.) Aug. 9, 1978 abstract.

Sasabe et al., "Dielectric Relaxations and Electrical Conductivities of Poly(alkyl Methacrylates) under High Pressure", J. Polymer science 6 (1968) pp. 1401-1418.

Lambert, Thomas, et al., Localized Arterial Drug Delivery from a Polymer Coated Removable Metallic Stent: Kinetics and Bioactivity of Forskolin, Cedars-Sinai Medical Center, Los Angeles, CA., *Circulation*, vol. 88, No. 4, Part 2, Oct. 1993.

Dev, Vishva, et al., Kinetics of Drug Delivery to the Arterial Wall Via Polyurethane Coated Removable Nitinol Stent-Comparative Study of 2 Drugs, Cedars-Sinai Medical Center, Los Angeles, CA., *Circulation*, vol. 88, No. 4, Part 2, Oct. 1993.

Brown, L.R., et al., "Characterization of glucose-mediated insulin release from implantable polymers", J Pharm Sci Dec. 1996; 85 (12): 1341-1345.

Catz P; et al., "In vitro evaluations of transdermal levonorgestrel", Drug Des Deliv, May 1990; 6 (1): 49-60.

Edelman, E.R. et al., "C-myc in vasculoproliferative disease", Circ Res Feb. 1995; 76(2): 176-82.

Eliaz, R., et al., "Long-term protection against the effects of tumor necrosis factor by controlled delivery of the soluble p55 TNF receptor", Cytokine, Jun. 1996; 8(6): 482-7.

Flemmig, T.F., et al., "Adjunctive controlled topical application of tetracycline HCl in the treatment of localized persistent or recurrent periodontitis. Effects on clinical parameters and elastase-alphal-proteinase inhibitor in gingival crevicular fluid", J. Clin Periodontol Oct. 1996; 23 (10):914-21.

Folkman, J, "How the field of controlled-release technology began, and its central role in the development of angiogenesis research", Biomaterials, Nov. 1990; 11 (9): 615-8.

Friling, R., et al., "A role of transforming growth factor-beta 1 in the control of corneal neovascularization", In Vivo 10, 59-64 (1996).

Goodson, J.M., et al., "Clinical responses following periodontal treatment by local drug delivery", J Periodontal Nov. 1985; 56 (11 Suppl): 81-7.

Huland, E., et al., "In vivo system to detect long-term continuous release of bioactive interleukin-2 by immunopharmacological depot preparations in nude mice with human tumors", J. Cancer Res. Clin. Oncol. (1995) 121:285-290.

Jafary, F, et al., "Point-Counterpoint: Drug Eluting Stent Euphoria: A Revolutionary Step or Misguided Euphoria?" http://www.medscape.com/viewarticle/442687, printed Oct. 15, 2002.

Klugherz, et al., "Twenty-eight-day Efficacy and Phamacokinetics of the sirolimus-eluting stent", Coronary Artery Disease, 2002, vol. 13, No. 3, pp. 183-188.

Lees, V.C., et al., "Angiogenesis in a delayed revascularization model is accelerated by angiogenic oligosaccharides of hyaluronan", Lab Invest, 1995, vol. 73, No. 73, No. 9, pp. 259-266.

Lesser, G.J., et al., "In vitro and in vivo studies of subcutaneous hydromorphone implants designed for the treatment of cancer pain", Pain, May-Jun. 1996; 65 (2-3): 265-72.

Lopez, J.J., et al., "Angiogenic potential of perivascularly delivered aFGF in a porcine model of chronic myocardial ischemia", Am J Physiol Mar. 1998; 274 (3 Pt 2): H930.

Morice et al., "A Randomized Comparison of a Sirolimus-Eluting Stent With a Standard Stent for Coronary Revascularaization" N. Engl. J. Med., vol. 346, No. 23, Jun. 6, 2002, pp. 1773-1780.

Ozaki, H., et al., "Intravitreal sustained release of VEGF causes retinal neovascularization in rabbits and breakdown of the blood-retinal barrier in rabbits and primates", Exp Eye Res, 1997, 64, 505-17.

Raman et al., "Coated Stents: Local Pharmacology", Semin. Intervent. Cardiol., 1998; 3:133-137.

Regar, et al., "Stent Development and Local Drug Delivery", British Medical Bulletin 2001; 59:227-248.

Sellke, F.W., et al., "Angiogenesis induced by acidic fibroblast growth factor as an alternative method of revascularization for chronic myocardial ischemia", Surgery Aug. 1996; 120 (2): 182-8.

Serruys, et al., "Rapamycin Eluting Stent: the Onset of a New Era in Interventional Cardiology", Heart 2002; 87:305-307.

Suzuki, T. et al., "Stent-based delivery of sirolimus reduces neointimal formation in a porcine coronary model", Circulation, 2001; 104: 1188-1193.

Whelan et al., "Mechanisms of Drug Loading and Release Kinetics", Semin. Intervent. Cardiol., 1998; 3:127-131.

Virmani, R., MD et al., "Mechanism of Late In-Stent Restenosis After Implantation of a Paclitaxel Derivate-Eluting Polymer Stent System in Humans", Circulation, 2002; 106:2649-2651.

Grube, E., MD, et al., "Six- and Twelve-Month Results From a Randomized, Double-Blind Trial on a Slow-Release Paclitaxel-Eluting Stent for De Novo Coronary Lesions", Circulation, 2003; 107: 38-42.

Serruys, P., MD, PhD, "Final Action results (Actinomycin D) Test", (Sep. 2002).

Trevino, M., "Results for drug-eluting stents disappoint, Diagnostic Imaging Online", (Apr. 25, 2002), http://www.dimag.com/dinews/2002042501.shtml.

Jampel, H. D., MD, et al., "In Vitro Release of Hydrophobic Drugs From Polyanhydride Disks", Ophthalmic Surgery, Nov. 1991, vol. 22, No. 11, pp. 676-680.

Sousa, J. Eduardo, MD, PhD, et al., "Clinical Cardiology: New Frontiers, New Frontiers in Cardiology, Drug-Eluting Stents: Part I", Circulation 2003; 107:2274-2279.

Voisard, R., et al., "Suche nach neuen Strategien zur Verhutung von Restenosen nach Angioplatie: Der Effekt von Cytostatika auf die Migrationsfahigkeit von restenosierenden Plaquezellen des Menschen in vitro", Vasa Suppl. 1992; 35:132-33.

Kornowski, R., et al., Slow-Release Taxol Coated GRII Stents Reduc Neointima Formation in a Porcine Coronary In-Stent Restenosis Model.

Drachman, D., et al., Sustained stent-based delivery of paclitaxel arrests neointernal thickening and cell proliferation.

Hermans, W. R. M., MD, et al., Prevention of restenosis after percutaneous transluminal coronary angioplasty: The search for a "magic bullet", Am. Heart Journal, vol. 122, No. 1, pt. 1, 171-187.

O'Keefe, Jr., J., MD, et al. "Ineffectiveness of Colchicine for the Prevention of Restenosis After Coronary Angioplasty", JAAC, vol. 19, No. 7, Jun. 1992: 1597-1600.

Hirata, S., et al.; Inhibition of in Vitro Vascular Endothelial Cell Proliferation and In Vivo Neovascularization by Low-dose Methotrexate, *Arthritis and Rheumatism*, vol. 32, No. 9 (Sep. 1989), p. 1065-1073.

Coronary Artery Disease, vol. 3, No. 3, (Mar. 1992), pp. 237-248.

Lambert, T., et al., "A New Method for Arterial Drug Delivery via Removable Stent", *JACC* vol. 21 No. 2, 834-2, (Feb. 1993).

Cox, D., MD, et al., "Effect of local delivery of heparin and methotrexate on neointimal proliferation in stented porcine coronary arteries", Coronary Artery Disease, Mar. 1992: vol. 3, No. 3, pp. 237-248.

Pitt, C.G., et al., "Progress in Contraceptive Delivery Systems", (Hafez, E.S.E, van Os, W., editors, vol. 1, pp. 17-18, MTP Press, Lancaster (1980).

Bartoli, M., et al., "In vitro and in vivo antitumoral activity of free, and encapsulated taxol", *J. Microencapsulation*, vol. 7, No. 2, 191-197 (1990).

The 2$^{nd}$ International Coronary Stenting Summit, Mar. 1-2, 1991.

Cox, David A., et al., "Local Delivery of Heparin and Methotrexate Fails to Inhibit InVivo Smooth Muscle Cell Proliferation, *Supplement to Circulation*, Abstracts from the 64$^{th}$ Scientific Sessions," vol. 84, No. 4, Oct. 1991.

Shen et al., "Polymer-Supported Lipid Bilayers on Benzophenone-Modified Substrates", *Biomacromolecules 2001*, vol. 2, No. 1, pp. 70-79.

Canadian Office Action dated Aug. 11, 2008.

International Search Report mailed Nov. 5, 2003.

International Preliminary Examination Report dated Oct. 14, 2004.

Communication pursuant to Article 96(2) EPC from European Patent Office dated Dec. 5, 2005.

Communication pursuant to Article 96(2) EPC from European Patent Office dated Jun. 4, 2007.

Japanese Office Action dated May 30, 2006.

* cited by examiner

BIOACTIVE AGENT RELEASE COATING AND CONTROLLED HUMIDITY METHOD

This is a Continuation of application Ser. No. 10/175,210 filed Jun. 18, 2002 now U.S. Pat. No. 7,097,850.

TECHNICAL FIELD

In one aspect, the present invention relates to a process of treating implantable medical devices with coating compositions to provide the release of bioactive (e.g., pharmaceutical) agents from the surface of the devices under physiological conditions. In another aspect, the invention relates to the coating compositions, per se, and to devices or surfaces coated with such compositions. In yet another aspect, the invention relates to methods of coating compositions on devices.

BACKGROUND OF THE INVENTION

Many surgical interventions require the placement of a medical device into the body. While necessary and beneficial for treating a variety of medical conditions, the placement of metal or polymeric devices in the body gives rise to numerous complications. Some of these complications include: increased risk of infection; initiation of a foreign body response resulting in inflammation and fibrous encapsulation; and initiation of a wound healing response resulting in hyperplasia and restenosis. These, and other complications must be dealt with when introducing a metal or polymeric device into the body.

One approach to reducing the potential harmful effects of such an introduction is to attempt to provide a more biocompatible implantable device. While there are several methods available to improve the biocompatibility of implantable devices, one method which has met U.S. Pat. No. 5,221,698 and Sahatjian, U.S. Pat. No. 5,304,121. Still other patents describe methods for preparing coated intravascular stents via application of polymer solutions containing dispersed therapeutic material to the stent surface followed by evaporation of the solvent. This method is described in Berg et al, U.S. Pat. No. 5,464,650.

However, there remain significant problems to be overcome in order to provide a therapeutically significant amount of a bioactive compound on the surface of the implantable medical device. This is particularly true when the coated composition must be kept on the device in the course of flexion and/or expansion of the device during implantation or use. It is also desirable to have a facile and easily processable method of controlling the rate of bioactive release from the surface of the device.

Although a variety of hydrophobic polymers have previously been described for use as drug release coatings, Applicant has found that only a small number possess the physical characteristics that would render them useful for implantable medical devices which undergo flexion and/or expansion upon implantation. Many polymers which demonstrate good drug release characteristics, when used alone as drug delivery vehicles, provide coatings that are too brittle to be used on devices which undergo flexion and/or expansion. Other polymers can provoke an inflammatory response when implanted. These or other polymers demonstrate good drug release characteristics for one drug but very poor characteristics for another.

Some polymers show good durability and flexibility characteristics when applied to devices without drug, but lose these favorable characteristics when drug is added. Furthermore, often times the higher the concentration of drugs or the thicker the application of polymer to the device surface, the poorer the physical characteristics of the polymer become. It has been very difficult to identify a polymer which provides the proper physical characteristics in the presence with limited success is to provide the device with the ability to deliver bioactive compounds to the vicinity of the implant. By so doing, some of the harmful effects associated with the implantation of medical devices can be diminished. Thus, for example, antibiotics can be released from the surface of the device to minimize the possibility of infection, and antiproliferative drugs can be released to inhibit hyperplasia. Another benefit to the local release of bioactive agents is the avoidance of toxic concentrations of drugs which are sometimes necessary, when given systemically, to achieve therapeutic concentrations at the site where they are needed.

Although the potential benefits expected from the use of medical devices capable of releasing pharmaceutical agents from their surfaces is great, the development of such medical devices has been slow. This development has been hampered by the many challenges that need to be successfully overcome when undertaking said development. Some of these challenges are: 1) the requirement, in some instances, for long term release of bioactive agents; 2) the need for a biocompatible, non-inflammatory device surface; 3) the need for significant durability, particularly with devices that undergo flexion and/or expansion when being implanted or used in the body; 4) concerns regarding processability, to enable the device to be manufactured in an economically viable and reproducible manner; and 5) the requirement that the finished device be sterilizable using conventional methods.

Several implantable medical devices capable of delivering medicinal agents have been described. Several patents are directed to devices utilizing biodegradable or bioresorbable polymers as drug containing and releasing coatings, including Tang et al, U.S. Pat. No. 4,916,193 and MacGregor, U.S. Pat. No. 4,994,071. Other patents are directed to the formation of a drug containing hydrogel on the surface of an implantable medical device, these include Amiden et al, of drugs and one in which the drug delivery rate can be controlled by altering the concentration of the drug in the polymer or the thickness of the polymer layer.

Applicants have previously provided an implantable medical device that can undergo flexion and/or expansion upon implantation, and that is also capable of delivering a therapeutically significant amount of a pharmaceutical agent or agents from the surface of the device. Applicant's issued U.S. Pat. No. 6,214,901 and published PCT Application No. WO 00/55396 provide a coating composition that comprises at least one polyalkyl(meth)acrylate, as a first polymeric component and poly(ethylene-co-vinyl acetate)("pEVA") as a second polymeric component, and describe the use of such compositions for coating an implant surface using any suitable means, e.g., by dipping, spraying and the like.

While certainly suitable for their intended use, Applicants have found that devices coated with such compositions have the potential to exhibit properties with detectable, and undesirable, variability, for instance, when evaluated using an "accelerated bioactive release" test method, or a "bioactive agent elution" test method, as described herein. It would be helpful to find ways of affecting, and preferably controlling, the potential for such variability, in order to provide coated devices with uniform properties.

Various other references relate to the use of coatings to provide implantable medical devices with bioactive agents. See, for instance, US 20020007213, and published PCT Application Nos. WO 200187372, WO 200187373, WO 200187374, WO 200187375, WO 200187376, WO 200226139, WO 200226271, WO 200226281, WO 200187342, and WO 200187263

Finally, Applicant's corresponding US application, filed on a date even herewith and having Ser. No. 11/212930, describes the use of one or more aromatic poly(meth)acrylate polymers selected from the group consisting of polyaryl (meth)acrylates, polyaralkyl(meth)acrylates, and polyaryloxyalkyl(meth)acrylates as the first polymeric component in such a composition.

SUMMARY OF THE INVENTION

Figure 1:
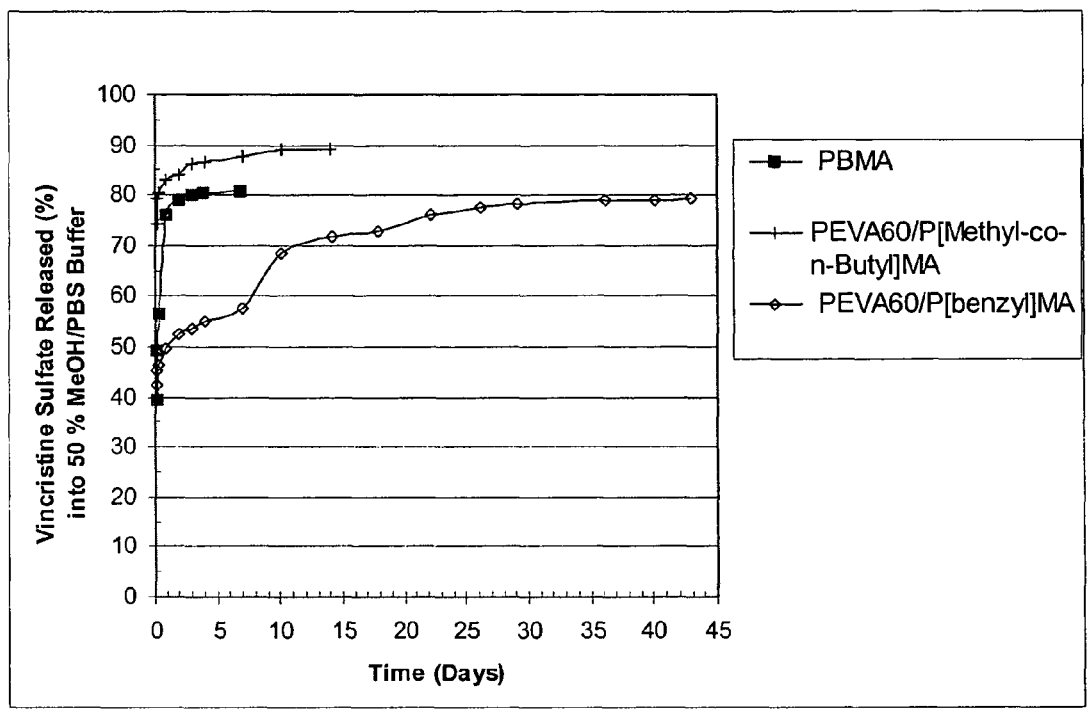
FIG. 1 provides a plot showing the experimental results described in Example 1.

The term "coating composition", as used herein, will refer to one or more vehicles (e.g., a system of solutions, mixtures, emulsions, dispersions, blends etc.) used to effectively coat a surface with bioactive agent, first polymer component and/or second polymer component, either individually or in any suitable combination. In turn, the term "coated composition" will refer to the effective combination, upon a surface, of bioactive agent, first polymer component and second polymer component, whether formed as the result of one or more coating vehicles, or in one or more layers. The present invention provides a coating composition, and related method for using the coating composition to coat a surface with a bioactive agent, for instance to coat the surface of an implantable medical device in a manner that permits the surface to release the bioactive agent over time when implanted in vivo. In a preferred embodiment, the device is one that undergoes flexion and/or expansion in the course of implantation or use in vivo. In a further preferred embodiment, the method of coating a device comprises the step of applying the composition to the device surface under conditions of controlled relative humidity (at a given temperature), for instance, under conditions of increased or decreased relative humidity as compared to ambient humidity.

Humidity can be "controlled" in any suitable manner, including at the time of preparing and/or using (as by applying) the composition, for instance, by coating the surface in a confined chamber or area adapted to provide a relative humidity different than ambient conditions, and/or by adjusting the water content of the coating or coated composition itself. In turn, even ambient humidity can be considered "controlled" humidity for purposes of this invention, if indeed it has been correlated with and determined to provide a corresponding controlled bioactive release profile.

Moreover, and particularly when coating a plurality of coating compositions (including components thereof) in the form of a corresponding plurality of layers, humidity can be controlled in different ways (e.g., using a controlled environment as compared to a hydrated or dehydrated coating composition) and/or at different levels to provide a desired release profile for the resulting coated composition. As described and exemplified below, a resultant composition can be coated using a plurality of individual steps or layers, including for instance, an initial layer having only bioactive agent (or bioactive agent with one or both of the polymeric components), over which are coated one or more additional layers containing suitable combinations of bioactive agent, first and/or second polymeric component, the combined result of which is to provide a coated composition of the invention. In turn, and in a particularly preferred embodiment, the invention further provides a method of reproducibly controlling the release (e.g., elution) of a bioactive agent from the surface of a medical device implanted in vivo, the method comprising the step of coating the device with a coating composition comprising the bioactive agent under conditions of controlled humidity. Applicants have discovered that coating compositions of this invention under conditions of increased humidity will typically accelerate release of the bioactive agent in vivo, while decreasing humidity levels will tend to decelerate release. The controlled humidity can be accomplished by any suitable means, e.g., by controlling humidity in the environment during the coating process and/or by hydrating the coating composition itself.

Moreover, a plurality of coating compositions and corresponding coating steps can be employed, each with its own controlled humidity, in order to provide a desired combination of layers, each with its corresponding release profile. Those skilled in the art will appreciate the manner in which the combined effect of these various layers can be used and optimized to achieve various effects in vivo.

While not intending to be bound by theory, the release kinetics of the bioactive agent in vivo are thought to generally include both a short term ("burst") release component, within the order of minutes to hours or less after implantation, and a longer term release component, which can range from on the order of hours to days or even months of useful release. As used herein, the "acceleration" or "deceleration" of bioactive release can include either or both of these release kinetics components.

In yet another embodiment, the present invention comprises a method for selecting an optimal release rate from a coated composition, the method comprising the steps of coating sample surfaces at a plurality of different humidity levels and evaluating the corresponding release profiles to determine a controlled humidity level corresponding to a desired profile. In a related embodiment, the invention provides a chamber for use in coating a medical device with a coating composition of the present invention under conditions of controlled humidity.

In one such embodiment, for instance, the coating composition is coated onto the device under relative humidity controlled at a level of between about 0% and about 95% relative humidity (at a given temperature, between about 15° C. and 30° C.), and more preferably between about 0% and about 50% relative humidity. Without intending to be bound by theory, Applicants have found that potential differences in the ambient humidity, as between coating runs at the same location, and/or as between different coating locations, can vary significantly, and in a manner that might affect such properties as the release or elution of the bioactive agent. By using a controlled humidity, Applicants can provide a coating in a manner that is significantly more controllable and reproducible.

Additionally, the ability to coat a device in the manner of the present invention provides greater latitude in the composition of various coating layers, e.g., permitting more or less of the polyalkyl(meth)acrylate and/or aromatic poly(meth) acrylate to be used in the coating composition used to form different layers (e.g., as a topcoat layer). This, in turn, provides the opportunity to further control release and elution of the bioactive agent from the overall coating.

A coating composition can be provided in any suitable form, e.g., in the form of a true solution, or fluid or paste-like emulsion, mixture, dispersion or blend. In turn, the coated composition will generally result from the removal of solvents or other volatile components and/or other physical-chemical actions (e.g., heating or illuminating) affecting the coated composition in situ upon the surface.

In a preferred embodiment the coated composition comprises at least one polyalkyl(meth)acrylate, as a first polymeric component and poly(ethylene-co-vinyl acetate) ("pEVA") as a second polymeric component. A particularly preferred polymer mixture for use in this invention includes mixtures of poly(n-butyl methacrylate)("pBMA") and poly(ethylene-co-vinyl acetate) co-polymers (pEVA). This mixture of polymers has proven useful with absolute polymer concentrations (i.e., the total combined concentrations of both polymers in the coating composition), of between about 0.05 and about 70 percent (by weight of the coating composition). In one preferred embodiment the polymer mixture includes a polyalkyl(meth)acrylate (such as poly(n-butyl methacrylate)) with a weight average molecular weight of from about 100 kilodaltons to about 1000 kilodaltons and a pEVA copolymer with a vinyl acetate content of from about 20 to about 40 weight percent.

In a particularly preferred embodiment the polymer mixture includes a polyalkyl(meth)acrylate (e.g., poly(n-butyl methacrylate)) with a weight average molecular weight of from about 200 kilodaltons to about 500 kilodaltons and a pEVA copolymer with a vinyl acetate content of from about 30 to about 34 weight percent. The concentration of the bioactive agent or agents dissolved or suspended in the coating mixture can range from about 0.01 to about 90 percent, by weight, based on the weight of the final coating composition.

As discussed in Applicant's co-pending application, coating compositions that include one or more aromatic poly(meth)acrylates as the first polymeric component, permit the use of a broad array of bioactive agents, particularly in view of the use of a corresponding broad array of solvents. For instance, such compositions of this invention permit the inclusion of polar bioactive agents, by the use of solvents and solvent systems that are themselves more polar than typically used. In such an embodiment, the composition preferably comprises at least one polymeric component selected from the group consisting of polyaryl(meth)acrylates, polyaralkyl(meth)acrylates, and polyaryloxyalkyl(meth)acrylates, and a second polymeric component comprising poly(ethylene-co-vinyl acetate). Such terms are used to describe polymeric structures wherein at least one carbon chain and at least one aromatic ring are combined with acrylic groups, specifically esters, to provide a coating composition of this invention. For instance, and more specifically, a polyaralkyl(meth)acrylate or polyarylalky(meth)acrylate is made from aromatic esters derived from alcohols also containing aromatic moieties.

Such compositions provide unexpected advantages in certain applications, even as compared to compositions that instead employ a polyalkyl(meth)acrylate. Such advantages relate, for instance, to the ability to provide coatings with different characteristics (e.g., different solubility characteristics) than other coated compositions (e.g., those that include a polyalkyl(meth)acrylate component), while maintaining an optimal combination of other desired properties. Without intending to be bound by theory, it would appear that the increased solubility (particularly in more polar solvents) that is provided by an aromatic, rather than alkyl poly(meth)acrylate of this invention, permits the use of poly(ethylene-co-vinyl acetate) components that are themselves more polar (e.g., having significantly greater vinyl acetate concentrations) than those typically preferred for use with the polyalkyl(meth)acrylates.

Suitable polymers, and bioactive agents, for use in preparing coating compositions of the present invention can be prepared using conventional organic synthetic procedures and/or are commercially available from a variety of sources, including for instance, from Sigma Aldrich (e.g., 1,3-dioxolane, vincristine sulfate, and poly(ethylene-co-vinylacetate), and Polysciences, Inc, Warrington, Pa. (e.g., polybenzylmethacryate and poly(methyl methacrylate-co-n-butyl methacrylate). Optionally, and preferably, such polymer components are either provided in a form suitable for in vivo use, or are purified for such use to a desired extent (e.g., by removing impurities) by conventional methods available to those skilled in the art.

The coating composition and method can be used to control the amount and rate of bioactive agent (e.g., drug) release from one or more surfaces of implantable medical devices. In a preferred embodiment, the method employs a mixture of hydrophobic polymers in combination with one or more bioactive agents, such as a pharmaceutical agent, such that the amount and rate of release of agent(s) from the medical device can be controlled, e.g., by adjusting the relative types and/or concentrations of hydrophobic polymers in the mixture. For a given combination of polymers, for instance, this approach permits the release rate to be adjusted and controlled by simply adjusting the relative concentrations of the polymers in the coating mixture.

A preferred coating composition of this invention includes a mixture of two or more polymers having complementary physical characteristics, and a pharmaceutical agent or agents applied to the surface of an implantable medical device which undergoes flexion and/or expansion upon implantation or use. The applied coating composition is cured (e.g., solvent evaporated) to provide a tenacious and flexible bioactive-releasing coated composition on the surface of the medical device. The complementary polymers are selected such that a broad range of relative polymer concentrations can be used without detrimentally affecting the desirable physical characteristics of the polymers. By use of the polymer mixtures of the invention the bioactive release rate from a coated medical device can be manipulated by adjusting the relative concentrations of the polymers.

DETAILED DESCRIPTION OF THE INVENTION

In a particularly preferred embodiment, the present invention relates to a coating composition and related method for coating an implantable medical device which undergoes flexion and/or expansion upon implantation. The structure and composition of the underlying device can be of any suitable, and medically acceptable, design and can be made of any suitable material that is compatible with the coating itself. The surface of the medical device is provided with a coating containing one or more bioactive agents.

In order to provide a preferred coating, a coating composition is prepared to include a solvent, a combination of complementary polymers dissolved in the solvent, and the bioactive agent or agents dispersed in the polymer/solvent mixture. The solvent is preferably one in which the polymers form a true solution. The pharmaceutical agent itself may either be soluble in the solvent or form a dispersion throughout the solvent. For instance, Applicant's previous U.S. Pat. No. 6,214,901 exemplifies the use of tetrahydrofuran as a solvent. While THF is certainly suitable, and at times is preferred, for certain coating compositions, Applicants have further discovered that other solvents can be used as well, in order to provide unexpected advantages. These solvents include, but are not limited to, alcohols (e.g., methanol, butanol, propanol and isopropanol), alkanes (e.g., halogenated or unhalogenated alkanes such as hexane and cyclohexane), amides (e.g., dimethylformamide), ethers (e.g., THF and dioxolane), ketones (e.g., methylethylketone), aromatic compounds (e.g., toluene and xylene), nitrites (e.g., acetonitrile) and esters (e.g., ethyl acetate).

The resultant coating composition can be applied to the device in any suitable fashion, under conditions of controlled relative humidity, e.g., it can be applied directly to the surface of the medical device, or alternatively, to the surface of a surface-modified medical device, by dipping, spraying, or any conventional technique. In one such embodiment, for instance, the coating comprises at least two layers, which are either coated under different conditions of relative humidity and/or which are themselves different. For instance, a base layer having either bioactive agent alone, or together with one or more of the polymeric components, after which one or more topcoat layers are coated, each with or without bioactive agent and/or each under different conditions of relative humidity. These different layers, in turn, can cooperate in the resultant composite coating to provide an overall release profile having certain desired characteristics, and is particularly preferred for use with bioactive agents of high molecular weight. Preferably, the composition is coated onto the device surface in one or more applications. The method of applying the coating composition to the device is typically governed by the geometry of the device and other process considerations. The coating is subsequently cured by evaporation of the solvent. The curing process can be performed at room temperature, elevated temperature, or with the assistance of vacuum.

The polymer mixture for use in this invention is preferably biocompatible, e.g., such that it results in no induction of inflammation or irritation when implanted. In addition, the polymer combination must be useful under a broad spectrum of both absolute concentrations and relative concentrations of the polymers. This means that the physical characteristics of the coating, such as tenacity, durability, flexibility and expandability, will typically be adequate over a broad range of polymer concentrations. Furthermore, the ability of the coating to control the release rates of a variety of pharmaceutical agents can preferably be manipulated by varying the absolute and relative concentrations of the polymers.

A first polymer component of this invention provides an optimal combination of various structural/functional properties, including hydrophobicity, durability, bioactive agent release characteristics, biocompatibility, molecular weight, and availability.

Further examples of suitable first polymers include polyaryl(meth)acrylates, polyaralkyl(meth)acrylates, and polyaryloxyalkyl(meth)acrylates, in particular those with aryl groups having from 6 to 16 carbon atoms and with weight average molecular weights from about 50 to about 900 kilodaltons. Examples of polyaryl(meth)acrylates include poly-9-anthracenylmethacrylate, polychlorophenylacrylate, polymethacryloxy-2-hydroxybenzophenone, polymethacryloxybenzotriazole, polynaphthylacrylate, polynaphthylmethacrylate, poly-4-nitrophenylacrylate, polypentachloro(bromo, fluoro)acrylate and methacrylate, polyphenylacrylate and methacrylate. Examples of polyaralkyl(meth)acrylates include polybenzylacrylate and methacrylate, poly-2-phenethylacrylate and methacrylate, poly-1-pyrenylmethylmethacrylate. Examples of polyaryloxyalkyl(meth)acrylates include polyphenoxyethylacrylate and methacrylate, polyethyleneglycolphenylether acrylates and methacrylates with varying polyethyleneglycol molecular weights.

A second polymer component of this invention provides an optimal combination of similar properties, and particularly when used in admixture with the first polymer component. Examples of suitable second polymers are available commercially and include poly(ethylene-co-vinyl acetate) having vinyl acetate concentrations of between about 8% and about 90%, in the form of beads, pellets, granules, etc. pEVA co-polymers with lower percent vinyl acetate become increasingly insoluble in typical solvents.

A particularly preferred coating composition for use in this invention includes mixtures of polyalkyl(meth)acrylates (e.g., polybutyl(meth)acrylate) or aromatic poly(meth)acrylates (e.g., polybenzyl(meth)acrylate) and poly(ethylene-co-vinyl acetate) co-polymers (pEVA). This mixture of polymers has proven useful with absolute polymer concentrations (i.e., the total combined concentrations of both polymers in the coating composition), of between about 0.05 and about 70 percent (by weight), and more preferably between about 0.25 and about 10 percent (by weight). In one preferred embodiment the polymer mixture includes a first polymer component (e.g., pBMA) with a weight average molecular weight of from about 100 kilodaltons to about 500 kilodaltons and a pEVA copolymer with a vinyl acetate content of from about 8 to about 90 weight percent, and more preferably between about 20 to about 40 weight percent. In a particularly preferred embodiment the polymer mixture includes a first polymer component with a molecular weight of from about 200 kilodaltons to about 400 kilodaltons and a pEVA copolymer with a vinyl acetate content of from about 30 to about 34 weight percent. The concentration of the bioactive agent or agents dissolved or suspended in the coating mixture can range from about 0.01 to about 90 percent, by weight, based on the weight of the final coating composition.

The bioactive (e.g., pharmaceutical) agents useful in the present invention include virtually any therapeutic substance which possesses desirable therapeutic characteristics for application to the implant site. These agents include: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives (including antiangiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

A coating composition of this invention can be used to coat the surface of a variety of devices, and is particularly useful for those devices that will come in contact with aqueous systems. Such devices are coated with a composition adapted to release bioactive agent in a prolonged and controlled manner, generally beginning with the initial contact between the device surface and its aqueous environment.

A coating composition of this invention is preferably used to coat an implantable medical device that undergoes flexion or expansion in the course of its implantation or use in vivo. The words "flexion" and "expansion" as used herein with regard to implantable devices will refer to a device, or portion thereof, that is bent (e.g., by at least 45 degrees or more) and/or expanded (e.g., to more than twice its initial dimension), either in the course of its placement, or thereafter in the course of its use in vivo.

Examples of suitable catheters include urinary catheters, which would benefit from the incorporation of antimicrobial agents (e.g., antibiotics such as vancomycin or norfloxacin) into a surface coating, and intravenous catheters which would benefit from antimicrobial agents and or from antithrombotic agents (e.g., heparin, hirudin, coumadin). Such catheters are typically fabricated from such materials as silicone rubber, polyurethane, latex and polyvinylchloride.

The coating composition can also be used to coat stents, e.g., either self-expanding stents, which are typically prepared from nitinol, or balloon-expandable stents, which are typically prepared from stainless steel. Other stent materials, such as cobalt chromium alloys, can be coated by the coating composition as well.

A coating composition of the present invention can be used to coat an implant surface using any suitable means, e.g., by dipping, spraying and the like. The suitability of the coating composition for use on a particular material, and in turn, the suitability of the coated composition can be evaluated by those skilled in the art, given the present description.

The overall weight of the coating upon the surface is typically not critical. The weight of the coating attributable to the bioactive agent is preferably in the range of about one microgram to about 10 mg of bioactive agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. More preferably, the weight of the coating attributable to the bioactive is between about 0.01 mg and about 0.5 mg of bioactive agent per $cm^2$ of the gross surface area of the device. This quantity of drug is generally required to provide adequate activity under physiological conditions.

In turn, the final coating thickness of a presently preferred coated composition will typically be in the range of about 0.1 micrometers to about 100 micrometers, and preferably between about 0.5 micrometers and about 25 micrometers. This level of coating thickness is generally required to provide an adequate concentration of drug to provide adequate activity under physiological conditions.

The coated composition provides a means to deliver bioactive agents from a variety of biomaterial surfaces. Preferred biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride. Examples of condensation polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to, titanium, stainless steel, and cobalt chromium. A second class of metals include the noble metals such as gold, silver, copper, and platinum. Alloys of metals may be suitable for biomaterials as well. The ceramics include, but are not limited to, silicon nitride, silicon carbide, zirconia, and alumina, as well as glass, silica, and sapphire. Combinations of ceramics and metals would be another class of biomaterials. Another class of biomaterials are fibrous or porous in nature. The surface of such biomaterials can be pretreated (e.g., with a Parylene coating composition) in order to alter the surface properties of the biomaterial.

Biomaterials can be used to fabricate a variety of implantable devices. General classes of suitable implantable devices include, but are not limited to, vascular devices such as grafts, stents, catheters, valves, artificial hearts, and heart assist devices; orthopedic devices such as joint implants, fracture repair devices, and artificial tendons; dental devices such as dental implants and fracture repair devices; drug delivery devices; ophthalmic devices and glaucoma drain shunts; urological devices such as penile, sphincter, urethral, bladder, and renal devices; and other catheters, synthetic prostheses such as breast prostheses and artificial organs. Other suitable biomedical devices include dialysis tubing and membranes, blood oxygenator tubing and membranes, blood bags, sutures, membranes, cell culture devices, chromatographic support materials, biosensors, and the like.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by the embodiments described by the language of the claims and the equivalents of those embodiments. Unless otherwise indicated, all percentages are by weight.

EXAMPLES

Test Methods

The potential suitability of particular coated compositions for in vivo use can be determined by a variety of methods, including the Durability, Flexibility and Release Tests, examples of each of which are described herein.

Sample Preparation

One millimeter diameter stainless steel wires (e.g. 304 grade) are cut into 5 centimeter lengths. The wire segments can be treated with a Parylene C coating composition (Parylene is a trademark of the Union Carbide Corporation) or evaluated with no treatment. The wire segments are weighed on a micro-balance.

Bioactive agent/polymer mixtures are prepared at a range of concentrations in an appropriate solvent, in the manner described herein. The coating mixtures are applied to respective wires, or portions thereof, by dipping or spraying, and the coated wires are allowed to cure by solvent evaporation. The coated wires are re-weighed. From this weight, the mass of the coating is calculated, which in turn permits the mass of the coated polymer(s) and bioactive agent to be determined. The coating thickness can be measured using any suitable means, e.g., by the use of a microprocessor coating thickness gauge (Minitest 4100).

The Durability and Flexibility of the coated composition can be determined in the following manner.

Durability Test

A suitable Durability Test, involves a method in which a coated specimen (e.g., wire) is subjected to repeated frictional forces intended to simulate the type of abrasion the sample would be exposed to in actual use.

The Test described below employs a repetitive 60 cycle treatment, and is used to determine whether there is any change in force measurements between the first 5 cycles and the last 5 cycles, or whether there is any observable flaking or scarring detectable by scanning electron microscopy ("SEM") analysis. Regenerated cellulose membrane is hydrated and wrapped around a 200 gram stainless steel sled. The cellulose membrane is clipped tightly on the opposite side of the sled. The sled with rotatable arm is then attached to a 250 gram digital force gauge with computer interface. The testing surface is mounted on a rail table with micro-stepper motor control. The wires are clamped onto the test surface. The cellulose covered sled is placed on top of the wires. Initial force measurements are taken as the sled moves at 0.5 cm/sec over a 5 cm section for 5 push/pull cycles. The sled then continues cycling over the coated samples for 50 push/pull cycles at 5 cm/sec to simulate abrasion. The velocity is then reduced to 0.5 cm/sec and the final force measurements are taken over another 5 push/pull cycles.

SEM micrographs are taken of abraded and nonabraded coated wires to evaluate the effects of the abrasion on the coating.

Flexibility Test

A suitable Flexibility Test, in turn, can be used to detect imperfections (when examined by scanning electron microscopy) that develop in the course of flexing of a coated specimen, and in particular, signs of cracking at or near the area of a bend.

A wire specimen is obtained and coated in the manner described above. One end of the coated wire (1.0 cm) is clamped in a bench vice. The free end of the wire (1.0 cm) is held with a pliers. The wire is bent until the angle it forms with itself is less than 90 degrees. The wire is removed from the vice and examined by SEM to determine the effect of the bending on the coating.

Bioactive Agent Release Assay

A suitable Bioactive Agent Release Assay, as described herein, can be used to determine the extent and rate of drug release under physiological conditions. In general it is desirable that less than 50% of the total quantity of the drug released, be released in the first 24 hours. It is frequently desirable for quantities of drug to be released for a duration of at least 30 days. After all the drug has been released, SEM evaluation should reveal an intact coating.

Except as otherwise provided herein, each coated wire is placed in a test tube with 5 ml of buffer, which unless stated otherwise herein, was provided in the form of Phosphate Buffered Saline ("PBS", 10 mM phosphate, 150 mM NaCl, pH 7.4, aqueous solution).

The tubes are placed on a rack in an environmental orbital shaker and agitated at 37° C. At timed intervals, the PBS is removed from the tube and replaced with fresh PBS. The drug concentration in each PBS sample is determined using the appropriate method.

After all measurable drug has been released from the coated wire, the wire is washed with water, dried, re-weighed, the coating thickness re-measured, and the coating quality examined by SEM analysis.

Comparative Example 1

Release of Hexachlorophene from Coated Stainless Steel Wires

A one millimeter diameter stainless steel wire (304 grade) was cut into two centimeter segments. The segments were treated with a Parylene C coating composition in order to deposit a thin, conformal, polymeric coating on the wires.

Four solutions were prepared for use in coating the wires. The solutions included mixtures of: pEVA (33 weight percent vinyl acetate, from Aldrich Chemical Company, Inc.); poly (n-butyl methacrylate "pBMA")(337,000 average molecular weight, from Aldrich Chemical Company, Inc.); and hexachlorophene ("HCP") from Sigma Chemical Co., dissolved in tetrahydrofuran. The solutions were prepared as follows:
1) 10 mg/ml pEVA//60 mg/ml pBMA//100 mg/ml HCP
2) 35 mg/ml pEVA//35 mg/ml pBMA//100 mg/ml HCP
3) 60 mg/ml pEVA//10 mg/ml pBMA//100 mg/ml HCP
4) 0 mg/ml pEVA//0 mg/ml pBMA//100 mg/ml HCP Nine wire segments were coated with each coating solution. The following protocol was followed for coating the wire segments. The Parylene-treated wire segments were wiped with an isopropyl alcohol dampened tissue prior to coating. The wire segments were dipped into the coating solution using a 2 cm/second dip speed. The wire segments were immediately withdrawn from the coating solution at a rate of 1 cm/second, after which the coated segments were air-dried at room temperature.

Individual wire segments were placed in tubes containing 2 ml of phosphate buffered saline ("PBS", pH 7.4). The tubes were incubated at 37 degrees centigrade on an environmental, orbital shaker at 100 rotations/minute. The PBS was changed at 1 hour, 3 hours, and 5 hours on the first day, and daily thereafter. The PBS samples were analyzed for HCP concentration by measuring the absorbance of the samples at 298 nms on a UV/visible light spectrophotometer and comparing to an HCP standard curve.

Results are provided in FIG. 1 of U.S. Pat. No. 6,214,901, which demonstrates the ability to control the release rate of a pharmaceutical agent from a coated surface by varying the relative concentrations of a polymer mixture.

Comparative Example 2

The polymers described in this disclosure have been evaluated using an Assay protocol as outlined above. The polymer mixtures evaluated have ranged from 100% pBMA to 100% pEVA. Representative results of those evaluations are summarized below.

Control coatings that are made up entirely of pBMA are very durable showing no signs of wear in the Durability Test. When subjected to the Flexibility Test, however, these coatings develop cracks, particularly in the presence of significant concentrations of drug. These coatings also release drug very slowly.

Control coatings that are made up entirely of pEVA, in contrast, are less durable and show no signs of cracking in the Flexibility Test, but develop significant scarring in the Durability Test. These coatings release drugs relatively rapidly, usually releasing more than 50% of the total within 24 hours.

The coatings, which contain a mixture of both polymers, are very durable, with no signs of wear in the Durability Test and no cracking in the Flexibility Test. Drug release from these coatings can be manipulated by varying the relative concentrations of the polymers. For instance, the rate of drug release can be controllably increased by increasing the relative concentration of pEVA.

Bioactive agent containing coatings which show no signs of scarring in the Durability Test and no cracking in the Flexibility Test possess the characteristics necessary for application to implantable medical devices that undergo flexion and/or expansion in the course of implantation and/or use.

Example 1

Three different polymer solutions, each at a concentration of 35 mg/ml, were prepared in 1,3-dioxolane in the manner provided below in order to provide coating compositions in the form of one part systems. The first solution contained poly(n-butyl methacrylate), with approximate weight average molecular weight of 337 kilodaltons; the second solution contained poly(ethylene-co-vinylacetate), with a vinyl acetate content of 60% (w/w) and poly(benzyl methacrylate) ("PEVA60/P[benzyl]MA"), in a polymer ratio of (50/50% w/w), respectively. The poly(n-butyl methacrylate) and poly(ethylene-co-vinylacetate) were purified by extraction with organic solvents to remove impurities, e.g., monomer residues. The third solution contained poly(ethylene-co-vinylacetate) with a vinyl acetate content of 60% (w/w) and poly(methyl methacrylate-co-n-butyl methacrylate)("PEVA60P[Methyl-co-n-Butyl]MA"), commercially available and known as poly(methyl methacrylate/n-butyl methacrylate), in a polymer ratio of (50/50% w/w), respectively. Vincristine sulfate and some additional 1,3-dioxolane were added to each of the three solutions in order to provide coating compositions in the form of one part systems (at final concentrations of 17.5 mg/ml). The vincristine/polymer ratio was 30/70% (w/w).

Sample Preparation

Sixteen-millimeter diameter stainless steel discs with an overall thickness of two millimeters were fabricated with a fourteen-millimeter diameter flat pedestal. The pedestal had a surface area of 1.54 cm$^2$. A surface treatment such as Parylene could be applied to the disc or the surface could be left untreated. The discs were weighed on a microbalance.

Polymer solutions containing vincristine sulfate were applied to the pedestal surface of the discs with a pipette. Two coats were applied with drying of the coat between applications. The solvent was evaporated from the discs and the discs were re-weighed on a microbalance to obtain the amount of vincristine sulfate per disc.

Bioactive Agent Release Assay

A suitable Bioactive Agent Release Assay, as described herein, can be used to determine the extent and rate of bioactive agent release. In general it is desirable that less than 50% of the total quantity of the bioactive agent be released in the first 24 hours. It is frequently desirable for quantities of bioactive agent to be released for a duration of at least 30 days.

Except as otherwise provided herein, each coated disc was placed in an amber vial with 4 mls of elution solvent. The elution solvent was composed of 50% methanol and 50% PBS. The vials were placed in a water bath and stirred at 37° C. At time intervals, the disc was removed from the vial, placed into a new vial containing fresh elution solvent and the new vial was placed into the water bath to continue the experiment. The bioactive agent concentration in each elution solvent sample was determined using UV spectroscopy.

After all measurable bioactive agent was released from the coated disc; the disc was washed with water, dried and re-weighed to determine the weight loss of the disc.

Conclusions

Results are provided in FIG. 1, where it can be seen that approximately 80% or more of the vincristine sulfate was released within 1 day for coatings that contained either poly(n-butyl methacrylate) or a blend of poly(methyl methacrylate-co-n-butyl methacrylate) and poly(ethylene-co-vinylacetate). The blend containing poly(benzyl methacrylate) and poly(ethylene-co-vinylacetate) showed sustained controlled release of vincristine sulfate for more than a one-month period.

Humidity Examples

Two examples are provided using two different bioactive agents, namely, β-estradiol, as an example of a low molecular weight bioactive agent that weighs 272 daltons, and tetramethylrhodamine isothiocyanate-Dextran (dextran-TRITC) as an example of a water soluble, high molecular weight bioactive agent that weighs 4400 daltons.

Example 2

Solution Preparation—Dextran

Two solutions were prepared in order to provide a coating composition of the presently claimed invention in the form of a two part system. The first solution was an aqueous solution containing the bioactive agent, dextran-TRITC, at a concentration of 15 mg/ml. The second solution contained poly(ethylene-co-vinylacetate) with a vinyl acetate concentration of 33% (w/w) and poly(n-butyl methacrylate), with approximate weight average molecular weight of 337 kilodaltons. The poly(n-butyl methacrylate) and poly(ethylene-co-vinylacetate) were purified by extraction with organic solvents to remove impurities, e.g., monomer residues. The polymers of the second solution were dissolved in tetrahydrofuran at a concentration of 10 mg/ml.

Sample Preparation

Fifteen-millimeter diameter stainless steel discs with an overall thickness of two millimeters were fabricated with a nine-millimeter diameter flat pedestal. The pedestal had a surface area of 0.64 cm$^2$. A surface treatment such as Parylene could be applied to the disc or the surface could be left untreated. The discs were weighed on a microbalance. The aqueous bioactive agent solution was applied to the pedestal surface of the discs with a pipette. The water evaporated from the discs and the discs were re-weighed on a microbalance to obtain the amount of the bioactive agent on the disc. The polymer coating solution containing poly(ethylene-co-vinylacetate) and poly(n-butyl methacrylate) was applied to the entire surface of the disc, covering the dextran. The polymer coating solution was coated under a range of humidity conditions. The tetrahydrofuran evaporated from the discs and the coatings were dried under vacuum. The discs were weighed a third time to obtain the amount of the polymer coating per disc.

Bioactive Agent Release Assay

A suitable Bioactive Agent Release Assay, as describe herein, can be used to determine the extent and rate of bioactive agent release under physiological conditions. In general it is desirable that less than 50% of the total quantity of the bioactive agent be released in the first 24 hours. It is frequently desirable for quantities of bioactive agent to be released for a duration of at least 30 days.

Except as otherwise provided herein, each coated disc was placed in an amber vial with 4 mls of PBS. The vials were placed in a water bath and stirred at 37° C. At time intervals, the disc was removed from the vial, placed into a new vial containing fresh PBS and the new vial was placed into the water bath to continue the experiment. The concentration of bioactive agent in each PBS sample was determined using UV spectroscopy.

After all measurable bioactive agent was released from the coated disc; the disc was washed with water, dried, and re-weighed to determine the weight loss of the disc.

Conclusion

Figure 2:
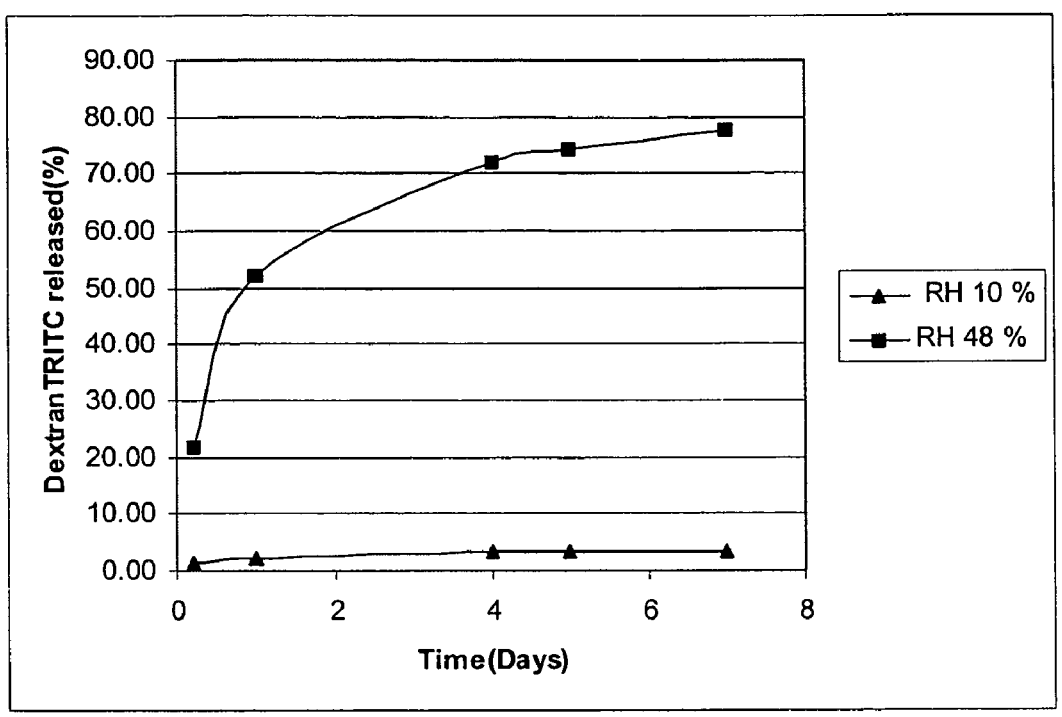
FIG. 2 provides a plot showing the experimental results described in Example 2.

The results are provided in FIG. 2 below, where it can be seen that the relative humidity at which the polymeric topcoat composition was coated can be used to control the release rate of the bioactive agent coated in an underlying layer. The bioactive agent was released at a faster rate from the composite coating where the topcoat was coated at 48% relative humidity than from the polymer topcoat coating that was coated at 10% relative humidity.

Example 3

Solution Preparation β-estradiol

A polymer coating solution containing poly(ethylene-co-vinylacetate) with a vinyl acetate concentration of 33% (w/w) and poly(n-butyl methacrylate) was prepared in tetrahydrofuran at a polymer ratio of 14/86% (w/w), respectively. β-estradiol was added to the polymer coating solution after dissolution of the polymer in order to provide a coating composition of the presently claimed invention in the form of a one part system. The bioactive agent/polymer ratio of the β-estradiol containing polymer solution was 30/70% (w/w) at a concentration of 10 mg/ml.

Sample Preparation

Eighteen-millimeter long, electropolished stainless steel stents with a 2 mm outer diameter were fabricated (Laserage Technology Corporation, Waukegan Ill.). A surface treatment such as Parylene could be applied to the stent or the surface could be left untreated. The stents were weighed on a microbalance. The β-estradiol containing polymer solution was coated (e.g., sprayed) onto stainless steel stents in an environment maintained at 0, 20, 30 or 40% relative humidity at 22° C. The stents were re-weighed after drying on a microbalance to obtain the amount of the β-estradiol per stent.

Bioactive Agent Release Assay

A suitable Bioactive Agent Release Assay, as described herein, can be used to determine the extent and rate of bioactive agent release under physiological conditions. In general it is desirable that less that 50% of the total quantity of the bioactive agent be released in the first 24 hours. It is frequently desirable for quantities of bioactive agent to be released for a duration of at least 30 days.

Except as otherwise provided herein, each coated stent was placed in an amber vial with 1.6 mls of PBS. The vials were placed in a water bath and stirred at 37° C. At time intervals, the stent was removed from the vial, placed into a new vial containing fresh PBS and the new vial was placed into the water bath to continue the experiment. The concentration of β-estradiol in each PBS sample was determined using TV spectroscopy.

Conclusion

Figure 3:
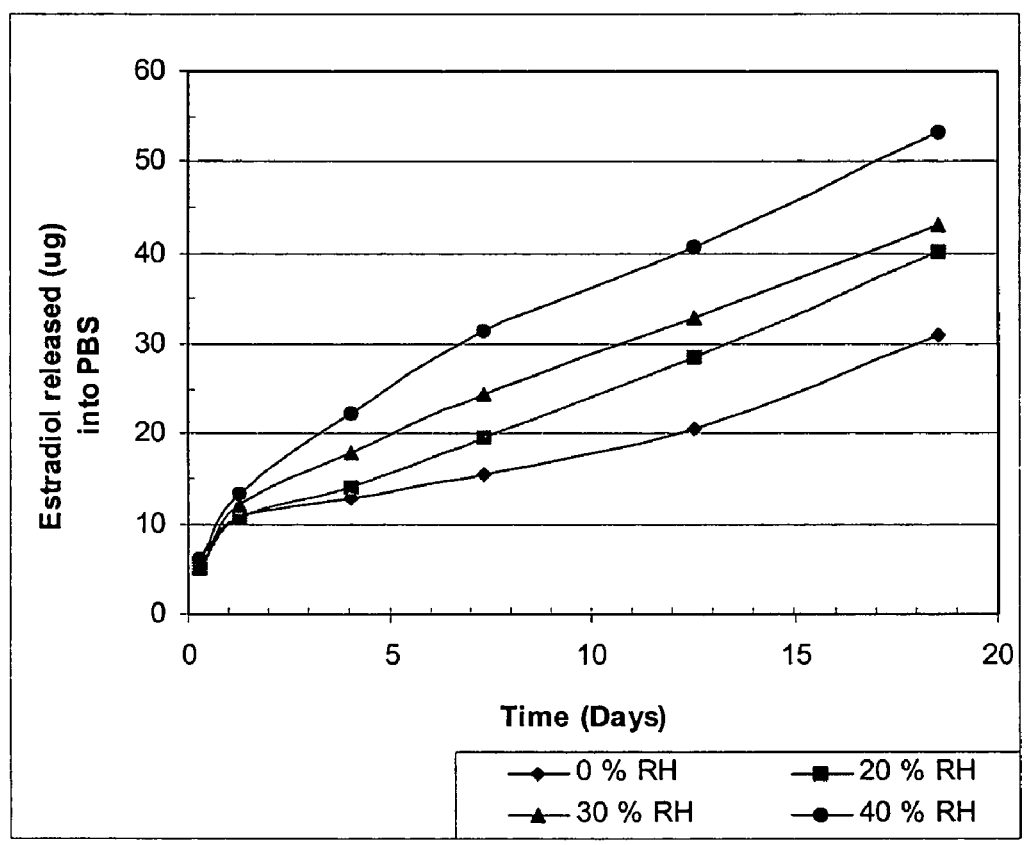
FIG. 3 provides a plot showing the experimental results described in Example 3.

The results are provided in FIG. 3 below, where it can be seen that the coating of the stents under different humidity level conditions can be used to control the β-estradiol rate of release from coatings containing poly(ethylene-co-vinylacetate) and poly(n-butyl methacrylate).

What is claimed is:

1. A method for adjusting the rate of release of a bioactive agent from a coating composition provided in vivo, the method comprising the steps of:
   a) providing the coating composition comprising a bioactive agent in combination with a plurality of polymers, including a first polymer component selected from the group consisting of polyalkyl(meth)acrylates and aromatic poly(meth)acrylates, and a second polymer component comprising poly(ethylene-co-vinyl acetate), and
   b) altering a humidity level in which the coating composition is applied to a surface of a medical device to adjust the bioactive agent release profile, whereby increasing the humidity level accelerates the release of the bioactive agent and decreasing the humidity level decelerates the release of the bioactive agent.

2. A method according to claim 1 wherein the aromatic poly(meth)acrylates are selected from the group consisting of polyaryl(meth)acrylates, polyaralkyl(meth)acrylates, and polyaryloxyalkyl(meth)acrylates, and humidity is altered by a method selected from the group consisting of controlling the humidity at which the device is coated with the coating composition, controlling the water content of the coating composition, or combinations thereof.

3. A method according to claim 1 wherein the first polymer component is selected from the group consisting of:
   polyaryl(meth)acrylates, polyaralkyl(meth)acrylates, and polyaryloxyalkyl(meth)acrylates with aryl groups having from 6 to 16 carbon atoms, the first polymer component having a weight average molecular weight of about 50 to about 900 kilodaltons, and wherein the vinyl acetate content is between about 20% and about 40% by weight.

4. A method according to claim 1 wherein the bioactive agent is selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

5. A method according to claim 1, the concentration of bioactive agent being about 0.01 to about 90 percent, by weight, based on the weight of the coating composition.

6. A method according to claim 1, the coating composition thickness being about 0.1 micrometers to about 100 micrometers.

7. A method for adjusting the rate of release of a bioactive agent from a coating composition provided in vivo, the method comprising the steps of:
- a) providing the coating composition comprising a bioactive agent in combination with a plurality of polymers, including a first polymer component selected from the group consisting of polyalkyl(meth)acrylates and aromatic poly(meth)acrylates, and a second polymer component comprising poly(ethylene-co-vinyl acetate), and
- b) accelerating the release of the bioactive agent in vivo by increasing a humidity level in which the coating composition is applied to a surface of a medical device.

8. A method according to claim 7 wherein the aromatic poly(meth)acrylates are selected from the group consisting of polyaryl(meth)acrylates, polyaralkyl(meth)acrylates, and polyaryloxyalkyl(meth)acrylates, and humidity is altered by a method selected from the group consisting of controlling the humidity at which the device is coated with the coating composition, controlling the water content of the coating composition, or combinations thereof.

9. A method according to claim 7 wherein the first polymer component is selected from the group consisting of:
- polyaryl(meth)acrylates, polyaralkyl(meth)acrylates, and polyaryloxyalkyl(meth)acrylates with aryl groups having from 6 to 16 carbon atoms, the first polymer component having a weight average molecular weight of about 50 to about 900 kilodaltons, and wherein the vinyl acetate content is between about 20% and about 40% by weight.

10. A method according to claim 7 wherein the bioactive agent is selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

11. A method according to claim 7, the concentration of bioactive agent being about 0.01 to about 90 percent, by weight, based on the weight of the coating composition.

12. A method according to claim 7, the coating composition thickness being about 0.1 micrometers to about 100 micrometers.

13. A method for adjusting the rate of release of a bioactive agent from a coating composition provided in vivo, the method comprising the steps of:
- a) providing the coating composition comprising a bioactive agent in combination with a plurality of polymers, including a first polymer component selected from the group consisting of polyalkyl(meth)acrylates and aromatic poly(meth)acrylates, and a second polymer component comprising poly(ethylene-co-vinyl acetate), and
- b) decelerating the release of the bioactive agent in vivo by decreasing the humidity level in which the coating composition is applied to a surface of a medical device.

14. A method according to claim 13 wherein the aromatic poly(meth)acrylates are selected from the group consisting of polyaryl(meth)acrylates, polyaralkyl(meth)acrylates, and polyaryloxyalkyl(meth)acrylates, and humidity is altered by a method selected from the group consisting of controlling the humidity at which the device is coated with the coating composition, controlling the water content of the coating composition, or combinations thereof.

15. A method according to claim 13 wherein the first polymer component is selected from the group consisting of:
- polyaryl(meth)acrylates, polyaralkyl(meth)acrylates, and polyaryloxyalkyl(meth)acrylates with aryl groups having from 6 to 16 carbon atoms, the first polymer component having a weight average molecular weight of about 50 to about 900 kilodaltons, and wherein the vinyl acetate content is between about 20% and about 40% by weight.

16. A method according to claim 13 wherein the bioactive agent is selected from the group consisting of thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, peptides, proteins, enzymes, extracellular matrix components, ACE inhibitors, free radical scavengers, chelators, antioxidants, anti polymerases, antiviral agents, photodynamic therapy agents, and gene therapy agents.

17. A method according to claim 13, the concentration of bioactive agent being about 0.01 to about 90 percent, by weight, based on the weight of the coating composition.

18. A method according to claim 13, the coating composition thickness being about 0.1 micrometers to about 100 micrometers.

* * * * *